United States Patent [19]

Esposito et al.

[11] Patent Number: 5,350,400
[45] Date of Patent: * Sep. 27, 1994

[54] MALLEABLE, BIOABSORBABLE, PLASTIC STAPLE; AND METHOD AND APPARATUS FOR DEFORMING SUCH STAPLE

[75] Inventors: Felix F. Esposito, Stratford; John A. Conners, Fairfield; Joseph N. Logan, Trumbull; James W. Dwyer, Brookfield, all of Conn.; Laurence Crainich, Charlestown, N.H.

[73] Assignee: American Cyanamid Company, Wayne, N.J.

[ * ] Notice: The portion of the term of this patent subsequent to Jan. 14, 2009 has been disclaimed.

[21] Appl. No.: 906,455

[22] Filed: Jun. 30, 1992

Related U.S. Application Data

[63] Continuation-in-part of Ser. No. 785,295, Oct. 30, 1991, abandoned.

[51] Int. Cl.⁵ .............................................. A61B 17/00
[52] U.S. Cl. ...................... 606/219; 227/902; 411/923; 411/457
[58] Field of Search ............... 606/219, 220; 227/19, 227/901, 902; 411/457, 923

[56] References Cited

U.S. PATENT DOCUMENTS

| | | |
|---|---|---|
| 4,809,695 | 3/1989 | Gwathmey et al. ................. 227/19 |
| 5,002,562 | 3/1991 | Oberlander ........................ 606/221 |
| 5,080,665 | 1/1992 | Jarrett et al. ..................... 606/219 |

FOREIGN PATENT DOCUMENTS

| | | |
|---|---|---|
| 0122046 | 10/1984 | European Pat. Off. ............ 606/221 |
| 0170512 | 2/1986 | European Pat. Off. ............ 606/219 |
| 1339394 | 12/1973 | United Kingdom ................ 227/902 |

Primary Examiner—Stephen C. Pellegrino
Assistant Examiner—Gary Jackson
Attorney, Agent, or Firm—Charles F. Costello, Jr.

[57] ABSTRACT

A malleable, bioabsorbable polymeric staple includes a back span with two legs depending perpendicularly therefrom that are deformed toward each other initially and then upwardly toward the back span such that end points on each leg extends to the side and past the back span. The staple has a noncircular cross-sectional shape. A surgical staple-deforming anvil for deforming the staples has a staple-receiving face formed with a pair of elongated, non-collinear pocket-like depressions each having an entry end lying on a longitudinal axis parallel to the back span of the staple, and an exit end. The respective exit ends of the pocket depressions are located on opposite sides of the longitudinal axis. Accordingly, the legs of a staple driven toward the anvil and received in the pocket depressions are initially bent toward each other and then steered upwardly toward opposite sides of the back span.

16 Claims, 8 Drawing Sheets

MALLEABLE, BIOABSORBABLE, PLASTIC STAPLE; AND METHOD AND APPARATUS FOR DEFORMING SUCH STAPLE

This is a continuation-in-part of U.S. Patent application Ser. No. 07/785,295, filed Oct. 30, 1991 now abandoned.

BACKGROUND OF THE INVENTION

1. Field Of the Invention

The present invention relates to surgical staples and to a method and an apparatus, particularly an anvil for a surgical stapling device, used to deform such staples to secure adjacent layers of tissue together. More specifically, this invention relates to the configuration of malleable, bioabsorbable, plastic or polymeric staples for suturing body organs and tissue, and to a precision-formed anvil for deforming the staples into that suturing configuration.

2. Description of the Prior Art

Historically, suturing of a surgical or other wound in organs and tissue has been done by hand. Conventional hand suturing techniques require a high degree of surgical skill. However, expertise in such techniques can vary widely from surgeon to surgeon, thereby resulting in widely varying quality in performance of the concluding steps of an operative procedure. In addition, even very skillful surgeons require a considerable amount of time to suture even relatively small wounds. Therefore, it is possible that an undesirable amount of blood may be lost during the suturing operation.

Accordingly, there has been an increasing tendency in recent years to use surgical staples to suture body organs and tissue after a medical procedure. Surgical staples have been particularly effective in suturing body organs and tissue such as the lung, as well as the esophagus, the stomach, the duodenum, and other body organs in the intestinal tract.

The advent of surgical stapling has provided several marked advantages over known hand suturing techniques. First, since one or more rows of surgical staples are inserted into tissue using a specially adapted instrument that is simply actuated, near uniformity of the closure from one surgeon to the next results. In addition, all staples in the closure are usually inserted simultaneously or in rapid sequence across the entire wound. Therefore, the closure is made very quickly to minimize loss of blood.

Surgical staples are usually mechanically inserted into tissue with surgical stapling instruments such as those known as anastomosis devices, including gastrointestinal anastomosis devices and transverse anastomosis devices. In such devices, the staples are loaded in one or more elongated rows into a magazine or cartridge. The magazine is then mounted in the device, which includes a mechanism for pushing, or driving, the staples from the magazine through two or more sections of tissue toward a deforming anvil. At the conclusion of the driving operation, the legs of each staple are conventionally clamped or bent, by engagement with the anvil, to a closed configuration to complete the suture and join the tissue sections together.

Gastrointestinal anastomosis-type devices drive and bend the staples aligned in a row one after the other in rapid sequence. Transverse anastomosis-type devices, drive and bend all staples in a row simultaneously.

One type of conventional staple 10, shown in FIG. 1, used with both gastrointestinal anastomosis and transverse anastomosis-type surgical stapling devices is made of a metal, like stainless steel or titanium, that is substantially inert in the body. The undeformed staple 10 or staple blank, is generally U-shaped and includes a back span 12 and two legs 14 depending perpendicularly from the back span in parallel to one another. Each leg 14 has a sharp chiseled end point 16 for cleanly piercing body organs or tissue. The metal staple blank is bent by having the legs engage and follow a conventional anvil to form a B-shaped closed staple 18 as shown in FIG. 2.

The anvil used to bend metal surgical staples is also formed of a hardened metal and includes a staple-bending face having a pair of coined or punched pockets located to oppose each staple in the magazine of the stapling device. The pockets are ordinarily elongated arcuate depressions, co-linearly arranged in parallel to the back span of a corresponding staple held in the magazine. Thus the anvil closely resembles the anvil of a conventional paper stapler.

When the staples 10 are driven from the magazine toward the anvil, the staple legs 14 each engage one pocket so that both legs are bent toward each other initially and thereafter upwardly toward the back span 12. Thus, as shown in FIG. 2, the end points 16 may come to rest against the underside of the back span 12.

Although metal staples inserted in the manner described above provide an effective and relatively simple means of suturing, one significant disadvantage is that they remain in the patient's body permanently. While generally not injurious to the body they may nevertheless interfere with post-operative X-ray or other diagnostic imaging of the patient.

This disadvantage can be overcome by using bioabsorbable polymeric staples that are degradable in the body after a short period of time. However, conventional polymeric staples are not malleable and thus cannot be easily bent into the B-shaped configuration shown in FIG. 2, to complete a suture. Therefore, as shown in FIG. 3, such conventional bioabsorbable staples instead are made in two parts, namely U-shaped polymeric staple body 20, the legs 22 of which are joined by a polymeric bar-like closure 24. The closure has two end point-receiving holes 26 that fit over the end points of the staple body 20 after they have pierced the tissue to be sutured. The staple body 20 and closure 24 are then forced toward each other to complete the suture.

While this two-part staple will dissolve in the body and, therefore, does not interfere with post-operative procedures, it has the drawback of requiring a part in addition to the basic staple blank and thus requires a more complicated mechanical stapling device for properly aligning the two parts and driving them together.

More recently, the assignee of the subject invention has made a breakthrough in the bioabsorbable staple field. Specifically as described in U.S. Pat. application Ser. Nos. 07/548,802, now U.S. Pat. No. 5,080,665, and 07/548,803, both filed Jul. 6, 1990, and U.S. patent application Ser. No. 07/799,521, filed Nov. 11, 1991 which are incorporated herein by reference, bioabsorbable or partially bioabsorbable surgical staples have been developed using polymeric materials. (Hereinafter the term "bioabsorbable" will be used generically to describe surgical staples of the type described in both of the applications mentioned above.) These staples retain all of the beneficial attributes of known bioabsorbable staples, but in addition are malleable or plastically deformable like metal staples. That is, these staples may be bent into complex shapes that are then retained. Therefore, they may be made of a single piece, not requiring independent staple body and closure parts.

Nevertheless, it has been found that if these new bioabsorbable staples are bent in the same way as are conventional metal staples, as shown in FIG. 2, so that the chiseled end points of the staple legs hit the back span, the points may crush or break.

Therefore, further improvement in surgical staples and devices for inserting them, taking advantage of the attributes of the new polymeric materials described above, are desirable.

SUMMARY OF THE INVENTION

Accordingly, it is a principle object of the present invention to enhance the benefits obtained by using malleable, bioabsorbable, polymeric staples in surgical stapling techniques.

It is a further object of the present invention to provide a malleable, bioabsorbable, polymeric staple deformed into a precise shape that securely joins tissue sections together with minimal tissue injury and damage to the staple itself.

It is another object of the present invention to provide a malleable bioabsorbable, polymeric staple having a cross-sectional shape that enhances tissue or clinching strength once deformed.

It is another object of the present invention to provide a high precision anvil for surgical stapling devices that will precisely and uniformly deform malleable, bioabsorbable, polymeric staples, as well as other staples, into a desired configuration.

It is yet another object of the present invention Lo provide a method for deforming the malleable, bioabsorbable, polymeric staple into the desired shape.

It is still another object of the present invention to provide a unique anvil that takes advantage of the beneficial properties of malleable, bioabsorbable, polymeric staples of the type described above to in turn provide an improved surgical stapling device.

These and other objects are achieved by the malleable, bioabsorbable, polymeric surgical staple of the present invention, which in a preferred embodiment comprises a back span, and first and second legs extending generally in the same direction from opposite ends of the back span, with the first and second legs having first and second end points, respectively. The first and second legs are deformed inwardly toward each other and upwardly toward the underside of the back span such that the end points of the respective legs extends past opposite sides of the back span.

In another preferred embodiment, the present invention comprises a method of deforming a malleable, bioabsorbable, polymeric staple wherein in an initial undeformed configuration the staple has a back span and first and second legs each having an end point and each extending in the same direction from opposite ends of the back span substantially perpendicularly thereto. The method includes the steps of initially deforming the first and second legs inwardly toward each other, and thereafter deforming the first and second legs upwardly such that the first and second end points extend past the back span of the staple on opposite sides thereof.

The polymeric surgical staple of the present invention also preferably has a noncircular oval or rectangular cross-sectional shape that enhances its ability to retain its deformed, tissue-joining configuration, as will be described in detail below.

In accordance with yet another aspect, a preferred embodiment of the invention is a surgical stapling device anvil for forming a staple having, in an undeformed state, a back span and first and second legs extending in the same direction from opposite ends of the back span substantially perpendicularly thereto. The anvil comprises a supporting body having a longitudinal axis and including a staple-receiving face, that may confront the end points of the legs of the staple. First and second pocket-like depressions are formed in the supporting body and each begins with an entry end located at the face, continues to a depressed portion within the body below the face, and terminates in an exit end at the face. The first and second pocket-like depressions extend in non-collinear relation with the entry end of each located substantially on the longitudinal axis and the exit end of each located on a side of the axis opposite the side on which the exit end of the other depression is located. The entry ends of the first and second depressions are spaced by a distance substantially equal to the distance between the depending legs of a staple blank. Accordingly, a staple such as described above driven toward this anvil will be deformed by first bending the staple legs toward each other and thereafter upwardly toward the back span. However, the end points of the legs will be steered toward opposite sides of the back span past the back span.

It will be appreciated, of course, that the surgical stapling device anvil configured in accordance with the present invention may be used with surgical staples of any material. However, because it is specifically designed for use with malleable, bioabsorbable, polymeric staples that are non-metallic, it may be made of plastic materials that are less expensive and in which the high precision pocket-like depressions may be more easily formed than known hardened metal anvils.

These and other objects, aspects, features, and advantages of the present invention will become apparent from the following detailed description of the preferred embodiments taken in conjunction with the drawings.

DETAILED DESCRIPTION OF THE PREFERRED EMBODIMENTS

As noted above, surgical staples in accordance with the present invention are made of an inventive polymeric or plastic material disclosed in detail in copending U.S. Pat. application Ser. No. 07/548,802, now U.S. Pat. Nos. 5,080,665, 07/548,803 and 07/799,521, which are incorporated herein by reference as noted above. Because they are made of this unique material, these staples are plastically deformable or malleable as well as bioabsorbable. The present invention takes advantage of these unique properties to provide a surgical staple having an improved deformed configuration, a method of deforming the staple to that configuration, and a surgical stapling device anvil, the use of which results in that configuration. Of course other bioabsorbable or partially bioabsorbable malleable polymeric staples later developed may be adapted to the present invention.

Figure 1:
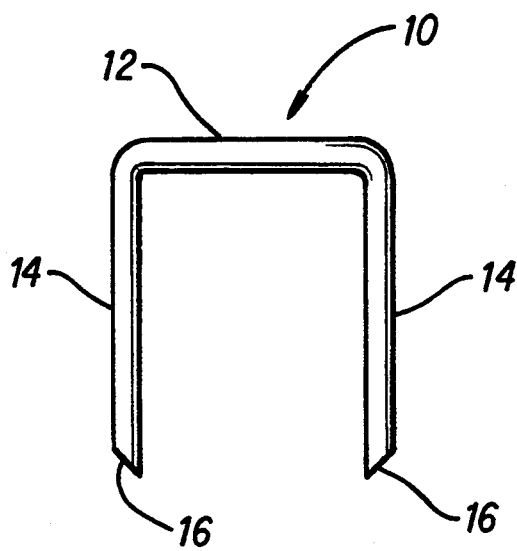
FIG. 1 a front elevational view of a conventional metal staple bank made, for example, of stainless steel or titanium.
Figure 2:
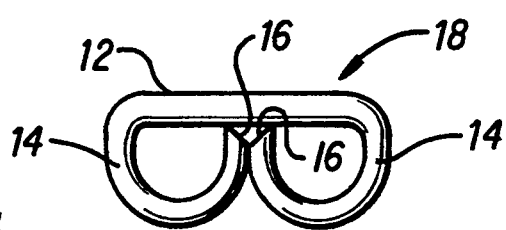
FIG. 2 is a front elevational view of a conventional, staple in a deformed configuration.
Figure 3:
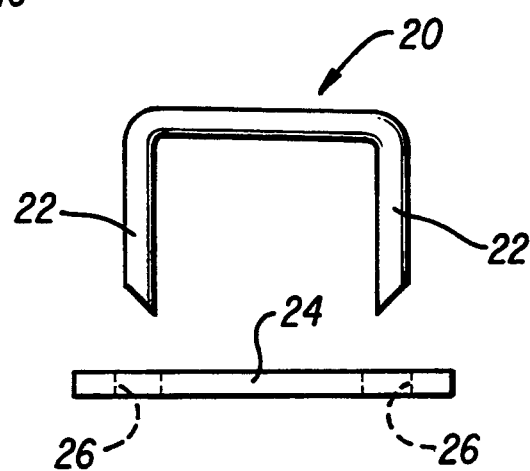
FIG. 3 is a front elevational view of a conventional two-piece bioabsorbable polymeric staple.
Figure 4:
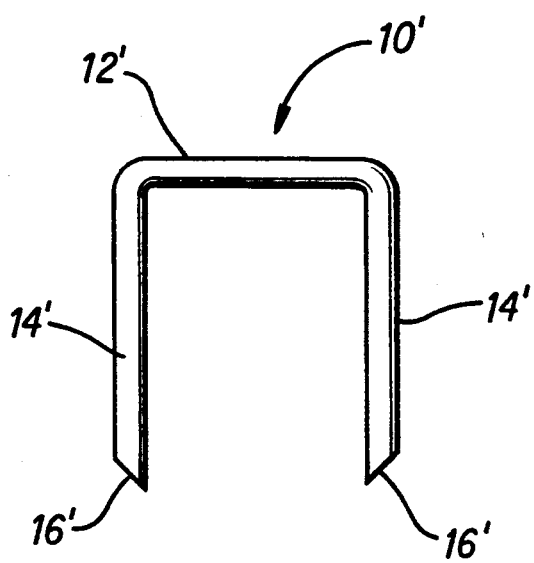
FIG. 4 is a front elevational view of a malleable, bioabsorbable, polymeric staple, which is not yet deformed, in accordance with the present invention.

More particularly, in its undeformed state shown in FIG. 4, the surgical staple or staple blank 10' in accordance with the present invention is generally U-shaped as are conventional staples shown in FIG. 1. Thus the improved staple 10' also includes a back span 12', two legs 14', and an end point 16' formed at the extreme of each leg 14'. The end points are sharply chiseled to cleanly pierce the body organs or tissue to be sutured. However, while the polymeric staple is malleable, the end points may be brittle and can break or crush if pressed against a hard surface.

Figure 5:
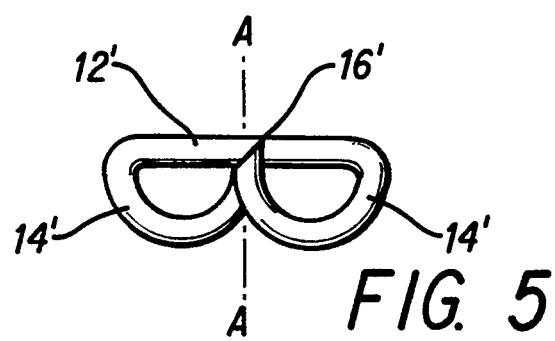
FIG. 5 is a front elevational view of a malleable, bioabsorbable, polymeric staple in accordance with the present invention deformed to a shape for suturing adjacent tissue sections together.
Figure 6:
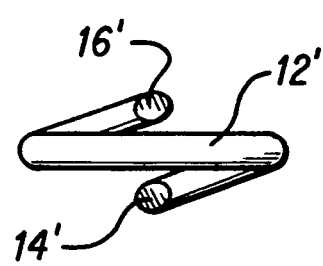
FIG. 6 is a top plan view of the staple shown in FIG. 5 in its deformed state.

FIGS. 5 and 6 show the plastic staple 10' in accordance with the present invention in its deformed state. As can be seen there, the legs 14' are bent from their configuration perpendicular to the back span 1240 into an arcuate shape with the end points 16' extending toward opposite sides of the back span 12' Thus the brittle end points 16' do not encounter the underside of the back span 12' during deformation and breaking or crushing of them is mitigated. Preferably, one end point 16' is guided toward one side of the back span and the other end point is guided toward the other side of the back span to further prevent the end points from engaging each other. The end points may desirably be closely adjacent opposite sides of the back span and may extend beyond or past the backspan. The end points can also be bent so that each extends in an opposite direction across an axial plane A—A perpendicular to the back span 12' of the staple.

While FIG. 6 described above and FIG. 17 to be described below illustrate the surgical staple of the present invention as having a generally circular cross-section, it is preferred that cross-section be noncircular, for example, oval or rectangular, at least in the regions where the staple is to be bent.

More particularly, it is known that the flexural rigidity of a beam may be defined as E x I where E is the modules of elasticity of the beam material and I is the moment of inertia. I is determined by the cross-sectional shape of the beam. Therefore, beam stiffness can be controlled by-appropriately determining the cross-sectional beam shape.

Using these principles, in one form the polymerical staple of the present invention has an oval cross sectional shape equal in cross-sectional area to a metal staple having a conventional circular cross-section, resulting in a 30 percent increase in beam stiffness without a resulting increase in the size of the tissue puncture area.

In greater detail, surgical polymeric staples that would otherwise be circular might arbitrarily have a diameter equal to about 0.018 inch or a cross-sectional area A given as follows:

$$A = \pi \frac{d^2}{4} = 2.545 \times 10^{-4} \text{ inch}^2. \tag{1}$$

The moment of inertia I of such a staple is given by:

$$I = \pi \left( \frac{d^4}{64} \right) \tag{2}$$
$$= 5.15 \times 10^{-9}$$

Figure 6A:
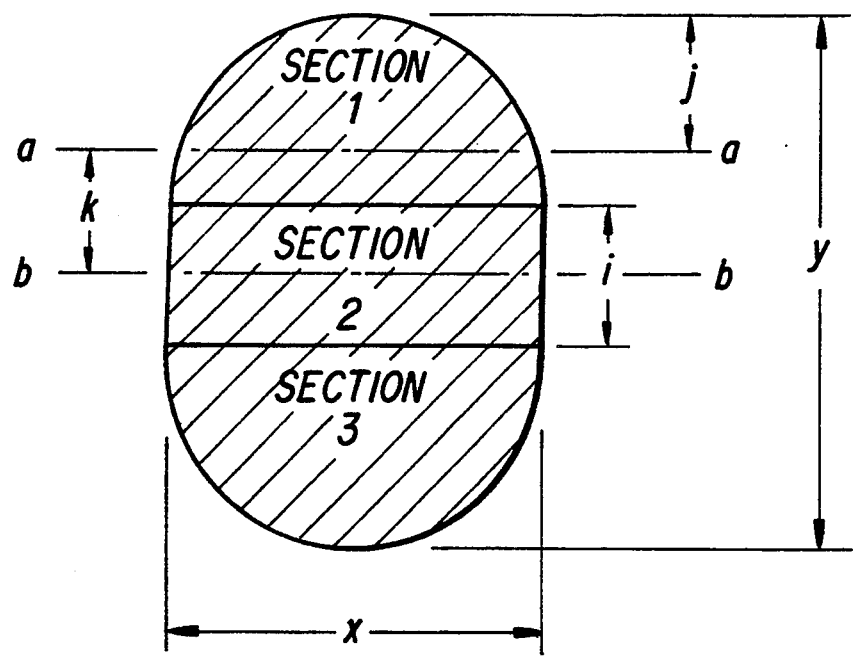
FIG. 6A is a detailed cross-sectional view of one particular embodiment of the staple shown in FIG. 5.
Figure 6B:
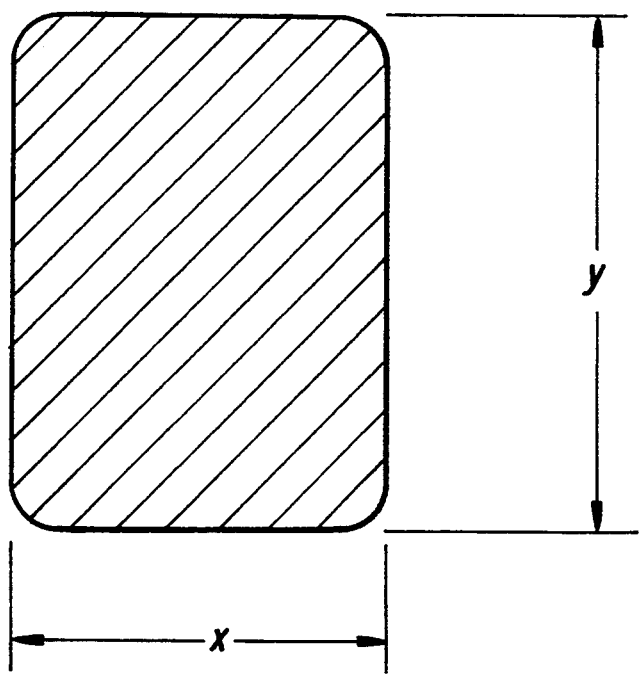
FIG. 6B is a detailed cross-sectional view of another embodiment of the staple shown in FIG. 5.

However, in accordance with one preferred embodiment of the present invention the cross-sectional shape is generally an oval as shown in FIG. 6A. The cross-sectional area is equal to the sum of the areas of sections 1, 2 and 3, or:

$$A_{oval} = \pi \left( \frac{x^2}{4} \right) + x(y - x) \tag{3}$$

Setting the cross-sectional area of the oval staple to be equal to the cross-sectional area of the round staple for the reasons stated above, and empirically setting x to be 0.015 inch, then y=0.0202 inch.

The moment of inertia $I_b$ of the staple of FIG. 6A about axis b-b, that is assuming the staple will be bent up and down as shown in that figure, is given by the sum of the moments of inertia about that axis of sections 1, 2, and 3.

The moment of inertia of section 2 about axis b-b is given by the known formula:

$$I_{b(2)} = xi^3/12 \qquad (4)$$
$$= (0.015)(0.0052)^3/12$$
$$= 1.758 \times 10^{-10}$$

where $i = y - x$.

The moment of inertia of each of sections 1 and 3 about axis b-b is given by:

$$I_{b(1,3)} = I_a + A_{(1,3)}k^2 \qquad (5)$$

where $I_a$ is given by the known formula:

$$I_a = 0.007x^4, \qquad (6)$$

$A_{(1,3)}$ equals the cross-sectional area of section 1 or 3; and k equals the distance from axis a-a, which is the neutral axis or center of mass of sections 1 or 3, to axis b-b.

k is given by:

$$k = (y/2) - j \qquad (7)$$

where $j = 0.288x$ in accordance with the known formula. Thus, $$I_a = 0.007x^4$$
$$= 3.544 \times 10^{-10}$$

$$I_{b(1,3)} = I_a + A_{(1,3)}k^2$$
$$= (3.544 \times 10^{-10}) +$$
$$(\pi x^2/8)\left[\left(\frac{0.0202}{2}\right) - (0.288)(.015)\right]^2$$
$$= (3.544 \times 10^{-10}) + (8.836 \times 10^{-5})(5.78 \times 10^{-3})^2$$
$$= 3.31 \times 10^{-9}$$

Accordingly, $I_{b(1,2,3)}$ for all three sections 1, 2, and 3 is $$I_{b(1,2,3)} = I_{b(1)} + I_{b(2)} + I_{b(3)} \qquad (8)$$
$$= 3.31 \times 10^{-9} + 1.758 \times 10^{-10} + 3.31 \times 10^{-9}$$
$$= 6.79 \times 10^{-9}$$

Comparing this value with that calculated using equation (2) for a staple having a round cross-section of equivalent area shows that the present invention achieves more than 30 percent greater beam stiffness than a staple having the circular cross-section of equivalent area.

Using the principles described above, polymeric surgical staples having other noncircular cross-sectional shapes than ovals are also possible. For example, another beneficial cross-sectional shape is the rectangle as shown in FIG. 65. In this embodiment, the moment of inertia I is given by $$I = xy^3/12 \qquad (9)$$

If $x = 0.015$ inch and $y = 0.0202$ inch, which are the nominal dimensions of the oval staple described above, then $$I = 1.03 \times 10^{\times 8}$$

This represents a 100 percent increase in beam stiffness above that provided by the comparable circular cross-section staple.

It is preferred that the aspect ratio of the minor dimension x to the major dimension y of the noncircular cross-section of the polymeric staple in accordance with the present invention be less than about 0.75. In the case described above, the aspect ratio is 0.74.

A precisely formed anvil in accordance with the present invention is used to guide the polymeric staple components with the accuracy necessary to locate the end points 16' adjacent the back span 12' on opposite sides thereof. The end points should be guided sufficiently close to the back span so the stapled body organ cannot work its way off of the end points.

Figure 7:
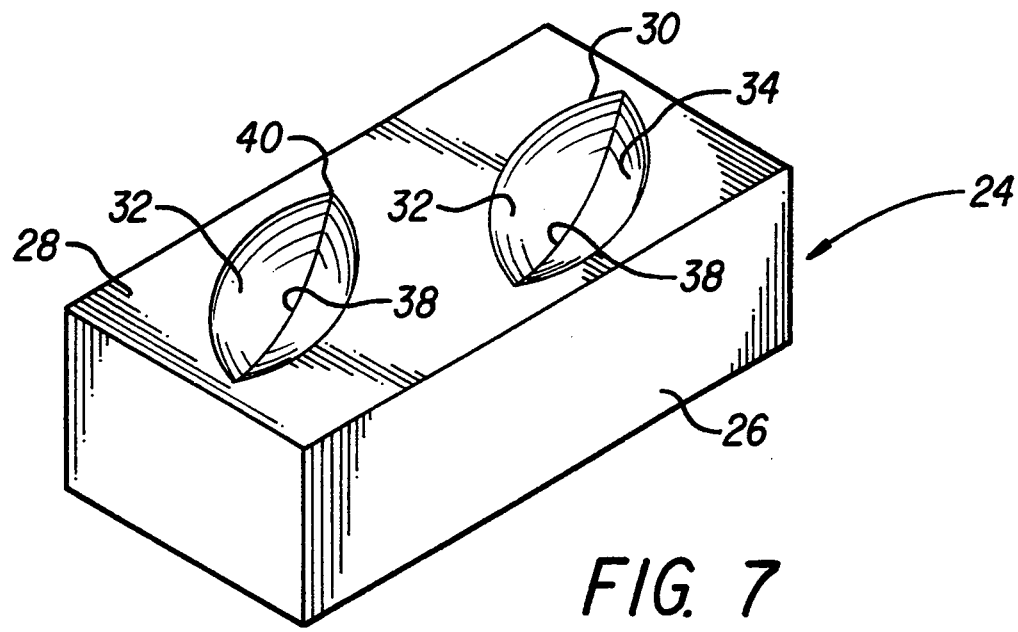
FIG. 7 is a schematic perspective view of a surgical stapling device anvil formed in accordance with one embodiment of the invention.
Figure 8:
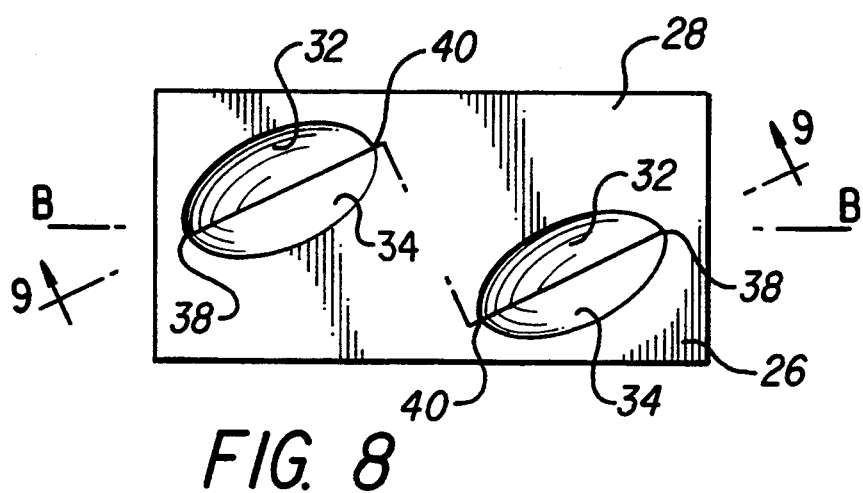
FIG. 8 is a schematic top plan view of the surgical stapling device anvil shown in FIG. 7.
Figure 9:
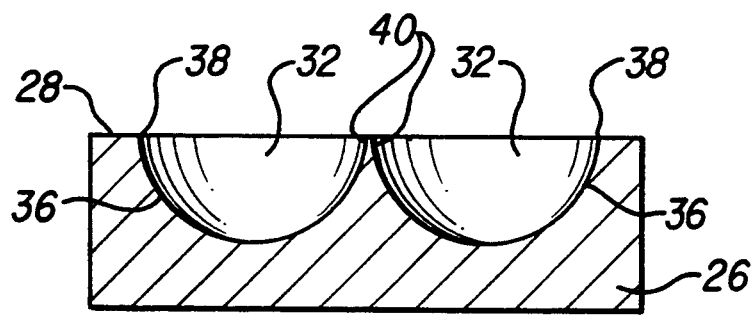
FIG. 9 is a vertical cross-sectional view of the surgical stapling device anvil shown in FIGS. 7 and 8, and taken on plane 9—9 in FIG. 8.
Figure 10:
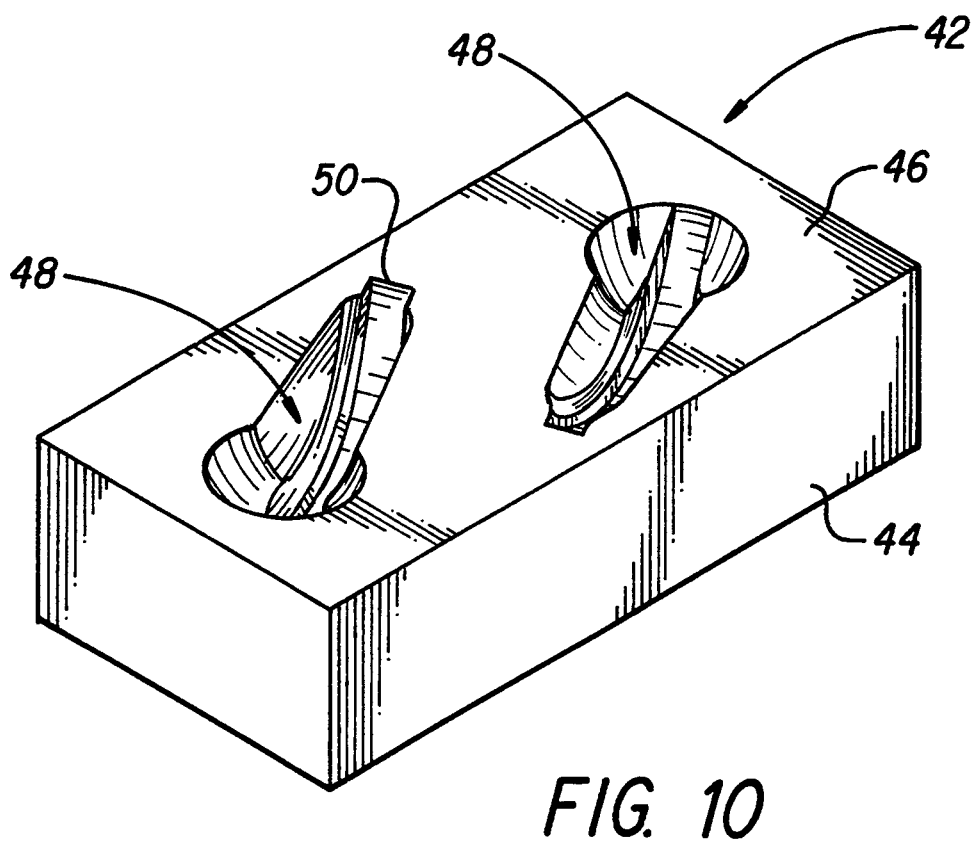
FIG. 10 is a schematic perspective view of a surgical stapling device anvil formed in accordance with another embodiment of the invention.

One such type of anvil 24 used to deform the polymeric staple in accordance with the present invention is shown in FIGS. 7 through 9. That anvil 24 has a supporting structure 26 having a staple-receiving face 28. The face and supporting structure can be either a one or multi-piece construction.

The face 28 includes two pockets 30 for receiving and guiding or steering the staple legs to the desired configuration.

It will be appreciated that while the anvil shown in FIGS. 7 through 9 includes but one pair of pockets 30, in the usual case an elongated row of pairs of such pockets would be formed in a similarly elongated support structure 26 so that a large number of surgical staples can be driven simultaneously or in rapid sequence.

Each pocket is defined by opposing first and second walls 32 and 34 which slope downwardly and inwardly toward each other to meet and form an endpoint guiding path 36. The guiding paths 36 curve from respective entry ends 38 to exit ends 40 in the face 28. As also can be seen in FIGS. 7 and 8 the entry end 38 of each path 36 is located substantially on the longitudinal axis B-B of the anvil 24, but the paths also curve from the entry ends in opposite directions so that the respective exit ends 40 lie on opposite sides of the longitudinal axis.

The anvil is arranged in the surgical stapling device so that the longitudinal axis B—B is substantially parallel to the back span of a staple to be driven toward the anvil. Moreover, the entry ends 38 of the respective paths 36 are spaced so as to receive the respective end points 16' of the legs 14' of the staple driven toward the anvil. Accordingly, when the staple is so driven, the end points 16' each first encounter the entry end 38 of one guide path 36. As driving of the staple toward the anvil continues, the end points 16' are steered along the curved guide paths 36 ultimately to be pointed past opposite sides of the staple back span 12' when driving is completed. The anvil pockets 30 further are of suitable depth relative to the length of the staple legs to achieve this result and so that the staple end points are finally located on opposite sides of the axial plane A—A of the staple as shown in FIGS. 5 and 6.

Thus it can be seen that the surgical stapling device anvil in accordance with the present invention will cause a malleable staple driven theretoward to assume as unique desired deformed configuration. Moreover, since this anvil is specifically designed to be used with malleable, bioabsorbable staples, which are made of polymeric material, it need not itself be made of a hardened material like metal. This factor is important because precisely shaped anvil pockets such as described above are difficult to form in hardened metal by other than very expensive machining techniques. Indeed coining or punching techniques for forming anvil pockets of conventional shape in known metal anvils are not suitable for forming the precisely shaped anvil pockets in accordance with the present invention. Thus plastics can be used to make the inventive anvil using precise yet inexpensive injection molding methods in the production process. Still further, plastics from which the anvil of the present invention may be made are themselves less expensive than metals used in conventional anvils. Therefore, the present invention provides significant advances over the prior art.

It has been found that polymeric materials like polycarbonate and liquid crystal polymer (LCP) may suitably be used for the inventive anvil.

FIGS. 10 through 17 show a surgical stapling device anvil in accordance with another embodiment of the present invention. This second anvil 42 differs from that shown in FIGS. 7 through 9 by providing a supporting structure 44 having a staple-receiving face 46 formed with alternatively shaped pocket-like depressions 48. More particularly, the face 46 includes two anvil pockets 48 each having a contoured staple-forming groove 50. The staple-forming grooves 50 extend in a direction parallel to each other but canted relative to the longitudinal axis C—C of the anvil so the staple legs when deformed are again offset to opposite sides of the back span of the staple.

Figure 11:
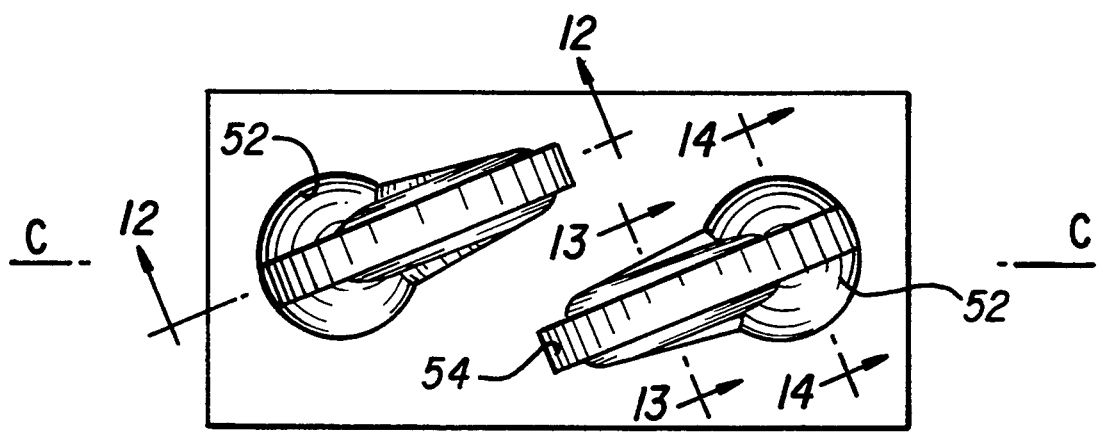
FIG. 11 is a schematic top view of the anvil shown in FIG. 10.
Figure 12:
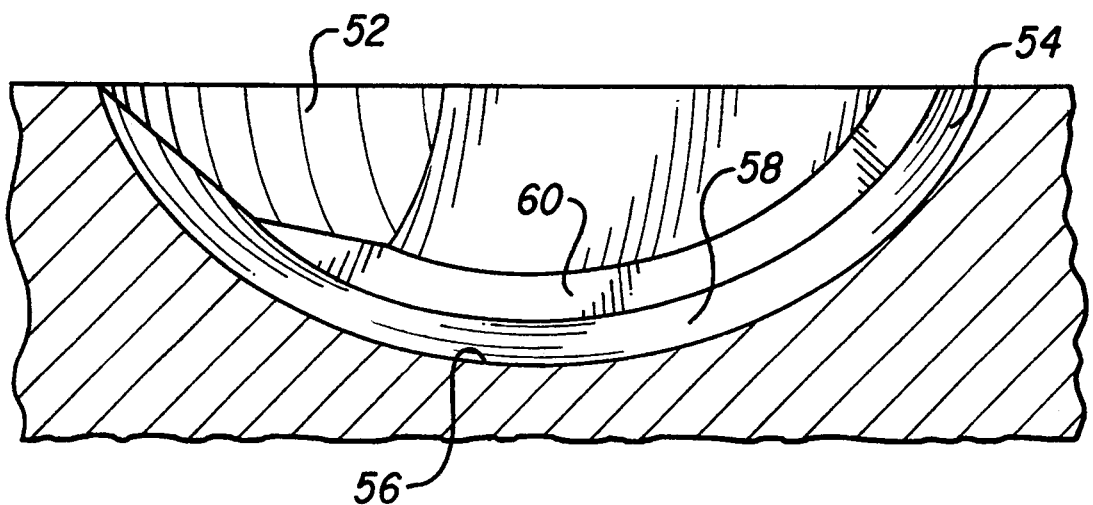
FIG. 12 is a vertical cross-sectional view of the anvil shown in FIG. 11 taken along plane 12—12.
Figure 13:
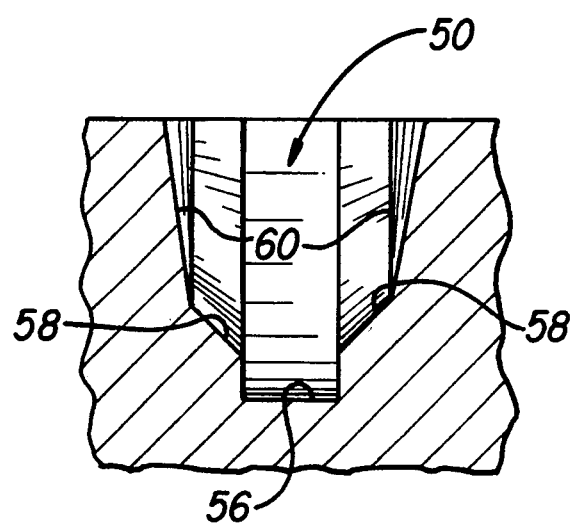
FIG. 13 is a vertical cross-sectional view of the anvil shown in FIG. 11 taken along plane 13—13.
Figure 14:
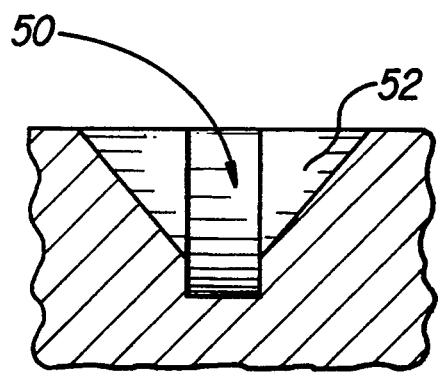
FIG. 14 a vertical is cross-sectional view of the anvil shown in FIG. 11 taken along plane 14—14.
Figure 15:
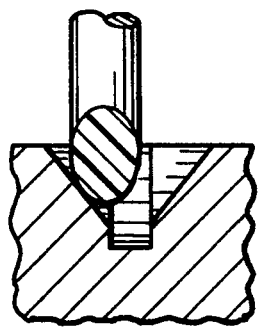
FIG. 15 is a vertical cross-sectional view similar to FIG. 14, showing a staple point being received and steered in an anvil pocket toward a desired position.
Figure 16:
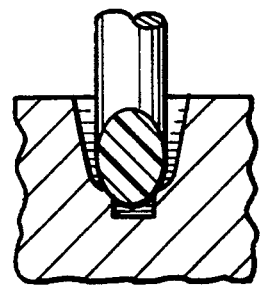
FIG. 16 is a vertical cross-sectional view similar to FIG. 15, showing the staple point properly aligned in the anvil to be steered to the desired position.
Figure 18:
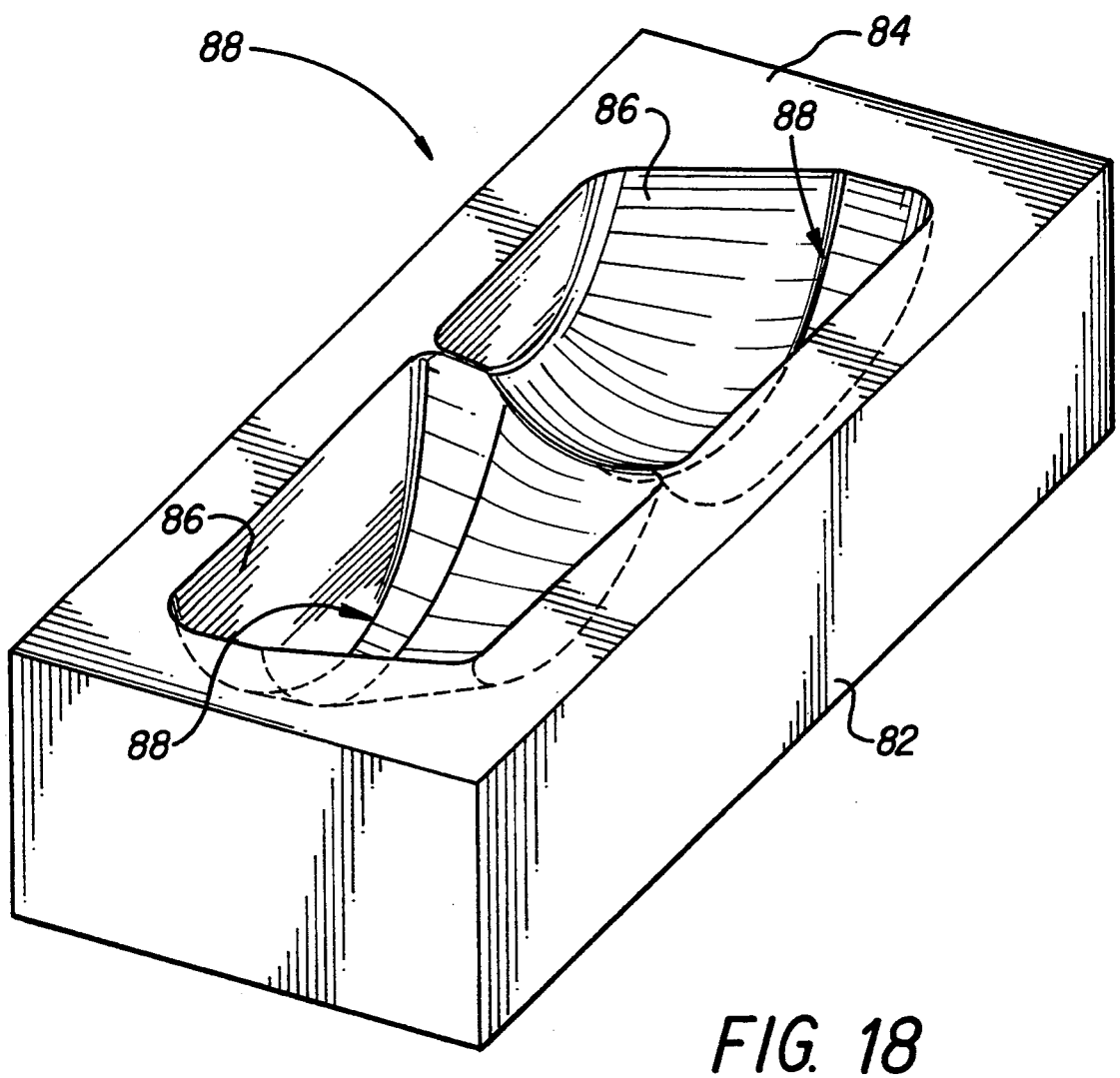
FIG. 18 is a schematic perspective view of a surgical stapling device anvil formed in accordance with yet another embodiment of the invention.

Each pocket has a generally arcuate longitudinal configuration, as shown in FIG. 12, that extends from a wide conical entry end 52 to a narrow exit end 54. That is, the conical entry end 52 has a diameter at the face 46 which is larger than the diameter of a staple leg and point as can be seen in FIG. 15, whereas the width of the exit end 54 should be smaller than the diameter of a staple leg or point as depicted in FIGS. 15 and 16. The bottom of the conical entry end 52 leads smoothly to the floor 56 of the pocket, which is defined by the staple guiding groove 50. At its center near its lowest section and extending toward the exit end, the groove 50 in each pocket is bounded on its lateral sides by stepped sloping walls 58 and 60 that narrow the pocket in that region as shown in FIGS. 11 and 13. As can be seen in FIG. 13 the surface 58 has a steeper slope than does the surface 60. Ultimately the groove 50 in each pocket terminates at the face in its exit end 54 which is the narrowest section of the pocket.

As can be seen in FIGS. 13 and 16, the floor 56 of the groove 50 lies significantly below the lower extreme of the surfaces 58. Thus the apex of the chiseled staple point is prevented from engaging and thereby digging into the floor 56.

Moreover, while the entry end 52 is relatively large, at the surface 46 it quickly necks down to a relatively narrow configuration. This arrangement minimizes "tenting" or pushing of tissue into the anvil pocket by a staple driven into the pocket.

Figure 17:
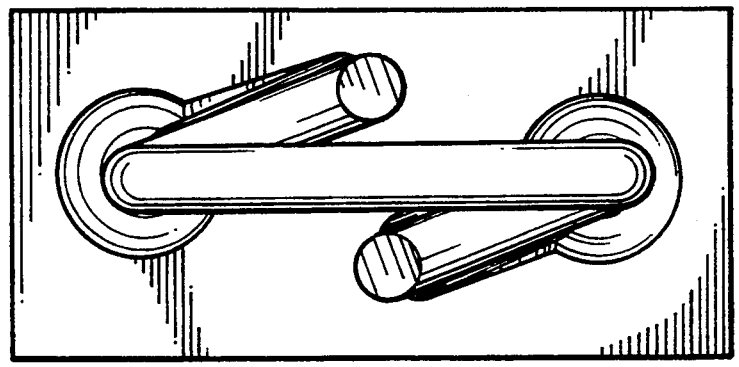
FIG. 17 is a top plan view of the anvil of FIGS. 10 through 14 and of a staple fully deformed thereby.

Thus it will be understood that this anvil configuration provides a relatively large target, the conical entry end 52, for each end point 16' of a staple leg 14' at the start of staple driving. The end point can be received in the entry end off center as shown in FIG. 15, so certain variations from staple to staple can be tolerated. However, as driving continues the staple end point is quickly guided to the groove 50 by the sloping walls 58 and 60 as shown in FIG. 16. Finally the end point is guided to exit from the groove itself at the exit end 54 of the pocket, without digging into the floor of the groove, as driving is completed, thereby to form the staple into the fully deformed configuration, as shown in FIG. 17.

Again, the anvil in accordance with this embodiment is arranged in the stapling device so that its longitudinal axis C—C is parallel to the back span of a staple held to be driven theretoward. Driving of the staple by the device toward the anvil may then proceed in the same way as described with reference to the embodiment shown in FIGS. 7 to 9.

Figure 19:
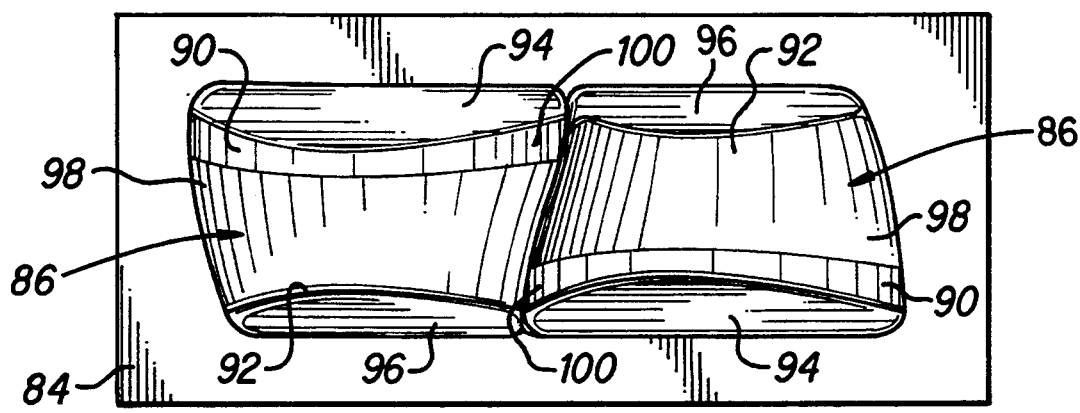
FIG. 19 is a schematic top view of the anvil shown in FIG. 18.

FIGS. 18 to 21 show a surgical stapling device anvil in accordance with yet another embodiment of the present invention. This third anvil 80 includes a supporting structure 82 having a staple receiving face 84 again formed with two pocket-like depressions 86 each having a contoured staple-forming groove 88. The staple-forming grooves 88 extend in directions generally longitudinally parallel to each other, but again offset relative to a longitudinal axis D—D of the anvil, as shown in FIG. 19, so the staple legs when deformed are offset to opposite sides of the back span of the staple.

Figure 20:
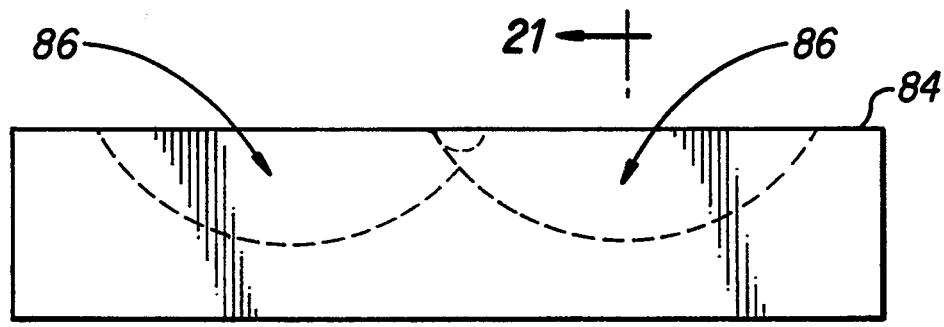
FIG. 20 is a schematic side elevational view of the anvil shown in FIG. 18.
Figure 21:
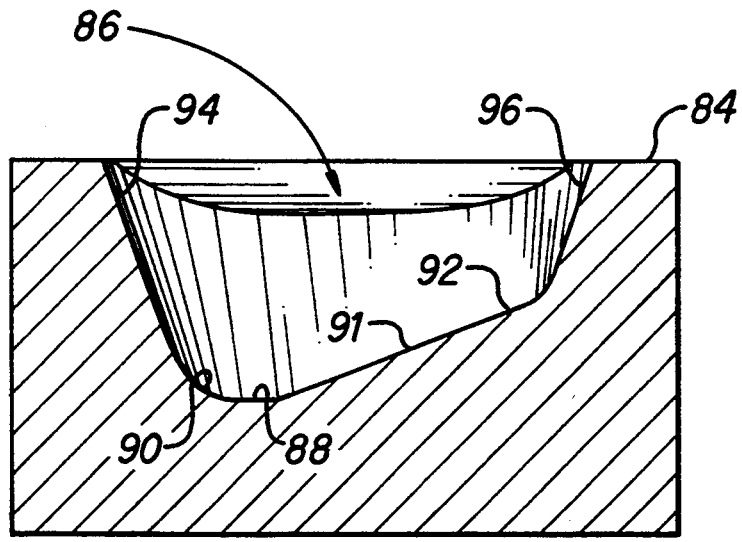
FIG. 21 is a vertical cross-sectional view of the anvil shown in FIGS. 18 to 20, taken along plane 21—21 in FIG. 20.

Each pocket-like depression 86 has an arculate longitudinal configuration in side elevation as shown in FIG. 20. Further, as shown in FIG. 21, each depression 86 also has a generally C-shaped lateral cross-section that has a portion 90 relatively deeply recessed to define the staple-forming groove 88. Each depression 86 then slopes gently at a wall 91 upwardly toward the receiving face 84 to a shallow portion 92. Finally, on each longitudinal side each depression slopes steeply upwardly toward the receiving face 84 at walls 94 and 96 from the deeply recessed portion 90 and shallow portion 92 respectively.

Thus it can be seen that each depression provides a large, wide target at opposing entry ends 98 so opposing end points of a staple can be received in the entry end 98, which is considered to be as wide as the depression 86 at this point, off center relative to the axis D—D. Nevertheless, the end point quickly is guided by the steep slopes 94 or 96 of the depressions 86 and the gentle slopes 91 to the deeply recessed portions 90 defining the staple-forming grooves 88. In this way, the end points are guided to positions oppositely laterally offset relative to the axis D—D to exit from the grooves 88 at exit ends 100 defined by inner terminations of the respective grooves 88, thereby to form the staple into the fully deformed configuration, again as shown in FIGS. 5 and 6.

As with the prior embodiments, the anvil in accordance with this one is arranged in the stapling device, so that its longitudinal axis D—D is parallel to the back span of a staple held to the driven theretoward so that deformation of the staple proceeds as described above.

As will be readily appreciated by those skilled in the art, the present invention provides marked improvements over known surgical staples and stapling device anvils. It achieves all of the benefits of known bioabsorbable, polymeric staples without the associate drawbacks. Moreover, by taking advantage of the unique properties of recently developed malleable, bioabsorbable, polymeric staples, this invention provides a unique deformed staple shape, as well as a unique surgical stapling device anvil structure and method for producing that shape.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A deformed malleable, polymeric surgical staple, comprising:
    a back span; and
    first and second legs extending in one direction from opposite ends of said back span, each of said first and second legs terminating in an end point; wherein
    said first and second legs are permanently deformed inwardly toward each other and toward said back span in a direction generally opposed to the one direction with each of said end points extending in the opposed direction toward at least one side of said back span.

2. The polymeric surgical staple according to claim 1, wherein said first leg, in the region of the end point thereof, is disposed on one side of said back span and said second leg, in the region of the end point thereof, is disposed on an opposite side of said back span.

3. The polymeric surgical staple according to claim 2, wherein the end points of said first and second legs respectively lie on opposite sides of a plane extending perpendicularly to said back span.

4. A polymeric surgical staple according to claims 1 to 3, wherein said first and second legs and said means for connecting said first and second legs each has a noncircular cross-section shape.

5. A polymeric surgical staple according to claim 4, wherein said noncircular cross-sectional shape is an oval.

6. A polymeric surgical staple according to claim 5, wherein the aspect ratio of the minor dimension of the cross-sectional shape to the major dimension thereof is less than about 0.75.

7. A polymeric surgical staple according to claim 4, wherein said noncircular cross-sectional shape is a rectangle.

8. A polymeric surgical staple according to claim 7, wherein the aspect ratio of the minor dimension of the cross-sectional shape to the major dimension thereof is less than about 0.75.

9. A deformable, malleable, polymeric surgical staple, comprising:
    a back span; and
    first and second legs extending in one direction from opposite ends of said back span, each of said first and second legs are permanently deformed and terminate in an end point;
    at least a portion of said back span, said first leg, and said second leg at which staple is deformable having a noncircular cross-sectional shape.

10. A polymeric surgical staple according to claim 9, wherein said noncircular cross sectional shape is an oval.

11. A polymeric surgical staple according to claim 10, wherein the aspect ratio of the minor dimension of the cross-sectional shape to the major dimension thereof is less than about 0.75.

12. A polymer surgical staple according to claim 9, wherein said noncircular cross-sectional shape is a rectangle.

13. A polymeric surgical staple according to claim 12, wherein the aspect ratio of the minor dimension of the cross-sectional shape to the major dimension thereof is less than about 0.75.

14. A method of deforming a malleable, polymeric surgical staple having a back span, first and second legs extending in one direction from opposite ends of the back span and substantially perpendicularly thereto in an undeformed state, the first and second legs each terminating in an end point; said method comprising the steps of:
    initially deforming the first and second legs inwardly toward each other;
    thereafter deforming the first and second legs toward the back span in a direction generally opposed to the one direction to cause the end points respectively of the first and second legs to extend in the opposed direction past the back span.

15. The method of forming a polymeric surgical staple according to claim 14, further comprising the step of deforming the first leg so the end point thereof extends past one side of the back span and deforming the second leg so the end point thereof extends past an opposite side of the back span.

16. The method of forming a polymeric surgical staple according to claim 15, further comprising the step of deforming the first and second legs so that the end points respectively thereof extend across and lie on opposite sides of a plane perpendicular to the back span.

* * * * *